United States Patent
Asenjo et al.

(10) Patent No.: US 7,202,074 B2
(45) Date of Patent: Apr. 10, 2007

(54) PROTEIN AND NUCLEIC ACID SEQUENCE ENCODING A KRILL-DERIVED COLD ADAPTED TRYPSIN-LIKE ACTIVITY ENZYME

(75) Inventors: Juan A. Asenjo, Santiago (CL); Barbara A. Andrews, Santiago (CL); Fernando Reyes, Santiago (CL); Mauricio Salamanca, Santiago (CL); Luis Burzio, Santiago (CL)

(73) Assignee: University of Chile, Santiago (CL)

( * ) Notice: Subject to any disclaimer, the term of this patent is extended or adjusted under 35 U.S.C. 154(b) by 319 days.

(21) Appl. No.: 10/896,010

(22) Filed: Jul. 22, 2004

(65) Prior Publication Data

US 2006/0020124 A1    Jan. 26, 2006

(51) Int. Cl.
*C12N 9/64*   (2006.01)
*C12N 15/57*  (2006.01)
*C12N 15/70*  (2006.01)
*C12N 15/79*  (2006.01)
*C11D 3/386*  (2006.01)

(52) U.S. Cl. ............... 435/226; 435/69.1; 435/252.3; 435/320.1; 526/23.2; 510/300

(58) Field of Classification Search .......... None
See application file for complete search history.

(56) References Cited

U.S. PATENT DOCUMENTS

| 5,217,878 | A |   | 6/1993 | van Eekelen ............ 435/69.1 |
| 5,278,062 | A |   | 1/1994 | Samal et al. ............. 435/223 |
| 5,945,102 | A | * | 8/1999 | de Faire et al. ......... 424/94.63 |
| 6,030,612 | A | * | 2/2000 | de Faire et al. ......... 424/94.63 |
| 2005/0025722 | A1 | * | 2/2005 | Franklin ..................... 424/50 |

OTHER PUBLICATIONS

Schroder et al, EUR. J. Biochem. 267, 2000, pp. 1039-1049, Feb. 2000, Structural comparison of psychrophilic and mesophilic . . . .

* cited by examiner

*Primary Examiner*—Nashaat T. Nashed
*Assistant Examiner*—William W. Moore
(74) *Attorney, Agent, or Firm*—Jacobson Holman PLLC

(57) ABSTRACT

The present invention provides nucleic acid and corresponding amino acid sequences of two isoforms of cold adapted trypsin-like activity protein, insolated from antarctic marine origin, preferably from antarctic krill (*Euphausia superba*) that can be used in a variety of industrial contexts and commercial purposes including laundry detergents, food processing, drugs and skin care products. The invention also relates to nucleic acid constructs, vectors, and host cells comprising the nucleic acid sequences as well as methods for producing and using the cold adapted trypsin-like protein.

14 Claims, No Drawings

SEQUENCE LISTING

<160> NUMBER OF SEQ ID NOS: 17

<210> SEQ ID NO 1
<211> LENGTH: 798
<212> TYPE: DNA
<213> ORGANISM: Euphausia superba

<400> SEQUENCE: 1

| | | | | | |
|---|---|---|---|---|---|
| atgaagggat | ttgtgatctg | tctactggtt | gctggggcat | gcgctgcccc | cagcaggaag | 60 |
| cccaccttcc | gcaagggcct | caacaagatt | gtaggcggag | atgaggccgc | ccctggtgag | 120 |
| cttccctacc | aactcagctt | ccaggatctc | tcatatggcg | acccatggca | tttctgcggt | 180 |
| gcctccatct | acaatgagaa | ctgggctatc | tgcgctggac | actgtgttgc | tggagaggac | 240 |
| atgaacaacc | cagattactt | gcaggtcgtt | gctggtgagc | ataaccagga | catcgttgaa | 300 |
| ggcaatgagc | agaccatcat | cctgtccaag | atcatccaac | atgagggcta | caatgcattt | 360 |
| actgtctcca | atgacatatc | tgtcctccaa | ctgtctcaac | cctgactttt | aatgacttc  | 420 |
| gtccaggcca | ttcctctgcc | cgaagcaggc | catactgctt | ctggtgattg | tattgtctct | 480 |
| ggttggggca | ccacatctga | gggtggtaat | accccgagtg | tcctcatgaa | ggtcgctgtc | 540 |
| ccagttgtta | ctgatgaaga | atgcaccgat | gcctatggtg | agggtgagat | tctagactcc | 600 |
| atgatctgtg | caggactacc | tgaaggaggc | aaagactcct | gccagggaga | ttctggtggg | 660 |
| ccatttgctt | gctctgatac | tggctccccc | taccttgctg | gtgttgtatc | ttggggatac | 720 |
| ggatgtgcca | gacccaacta | cccaggtgtt | tacactgaag | tttcctactt | cgttgactgg | 780 |
| attatgacta | acaccgca   |            |            |            |            | 798 |

<210> SEQ ID NO 2
<211> LENGTH: 798
<212> TYPE: DNA
<213> ORGANISM: Euphausia superba

<400> SEQUENCE: 2

| | | | | | |
|---|---|---|---|---|---|
| atgaagggat | ttgtgatctg | tctactggtt | gctggggcat | gcgctgcccc | aagcaggaag | 60 |
| cccaccttcc | gcaggggcct | taacaagatt | gtaggcggag | atgaggccgc | ccccggtgag | 120 |
| cttccctacc | agctcagctt | ccaggatctc | tcatatgcg  | acccatggca | tttctgcggt | 180 |
| gcctccatct | acaatgagaa | ctgggccatc | tgcgctggac | actgtgttgc | tggagaggac | 240 |
| atgaacaacc | ctgattactt | acaggtcgtt | gctggtgagc | ataatcagga | catcgttgaa | 300 |
| ggcaatgagc | agaccatcat | cctgtccaag | atcatccaac | atgagggcta | caatgcattt | 360 |
| actgtctcca | atgacatatc | tgtactccaa | ctgtctcaac | cctgaccctt | caatgactac | 420 |
| gtccagccca | ttgcactgcc | cgaagctggc | catactgctt | ctggtgattg | tattgtctct | 480 |
| ggttggggca | ccacatctga | gggtggtaat | accccaagtg | tcctcatgaa | ggtcgctgtc | 540 |
| ccagttgtta | ctgatgaaga | atgcaccgat | gcctatggtg | agggtgagat | tctagactcc | 600 |
| atgatatgtg | caggactacc | cgaaggaggc | aaagactcct | gccagggaga | ttctggtggg | 660 |
| ccattcgctt | gctctgatac | tggctccccc | taccttgctg | gtgttgtatc | ttggggatac | 720 |
| ggatgtgcca | gacccaacta | cccaggtgtt | tacactgaag | tttcctactt | cgttgactgg | 780 |
| attatgacta | acaccgca   |            |            |            |            | 798 |

<210> SEQ ID NO 3
<211> LENGTH: 266

```
<212> TYPE: PRT
<213> ORGANISM: Euphausia superba

<400> SEQUENCE: 3

Met Lys Gly Phe Val Ile Cys Leu Leu Val Ala Gly Ala Cys Ala Ala
1               5                   10                  15

Pro Ser Arg Lys Pro Thr Phe Arg Lys Asp Leu Asn Lys Ile Val Gly
            20                  25                  30

Gly Asp Glu Ala Ala Pro Gly Glu Leu Pro Tyr Gln Leu Ser Phe Gln
        35                  40                  45

Asp Leu Ser Tyr Gly Asp Pro Trp His Phe Cys Gly Ala Ser Ile Tyr
    50                  55                  60

Asn Glu Asn Trp Ala Ile Cys Ala Gly His Cys Val Ala Gly Glu Asp
65                  70                  75                  80

Met Asn Asn Pro Asp Tyr Leu Gln Val Val Ala Gly Glu His Asn Gln
                85                  90                  95

Asp Ile Val Glu Gly Asn Glu Gln Thr Ile Ile Leu Ser Lys Ile Ile
            100                 105                 110

Gln His Glu Gly Tyr Asn Ala Phe Thr Val Ser Asn Asp Ile Ser Val
        115                 120                 125

Leu Gln Leu Ser Gln Pro Leu Thr Phe Asn Asp Phe Val Gln Ala Ile
    130                 135                 140

Pro Leu Pro Glu Ala Gly His Thr Ala Ser Gly Asp Cys Ile Val Ser
145                 150                 155                 160

Gly Trp Gly Thr Thr Ser Glu Gly Gly Asn Thr Pro Ser Val Leu Met
                165                 170                 175

Lys Val Ala Val Pro Val Val Thr Asp Glu Glu Cys Thr Asp Ala Tyr
            180                 185                 190

Gly Glu Gly Glu Ile Leu Asp Ser Met Ile Cys Ala Gly Leu Pro Glu
        195                 200                 205

Gly Gly Lys Asp Ser Cys Gln Gly Asp Ser Gly Gly Pro Phe Ala Cys
    210                 215                 220

Ser Asp Thr Gly Ser Pro Tyr Leu Ala Gly Val Val Ser Trp Gly Tyr
225                 230                 235                 240

Gly Cys Ala Arg Pro Asn Tyr Pro Gly Val Tyr Thr Glu Val Ser Tyr
                245                 250                 255

Phe Val Asp Trp Ile Met Thr Asn Thr Ala
            260                 265

<210> SEQ ID NO 4
<211> LENGTH: 266
<212> TYPE: PRT
<213> ORGANISM: Euphausia superba

<400> SEQUENCE: 4

Met Lys Gly Phe Val Ile Cys Leu Leu Val Ala Gly Ala Cys Ala Ala
1               5                   10                  15

Pro Ser Arg Lys Pro Thr Phe Arg Arg Gly Leu Asn Lys Ile Val Gly
            20                  25                  30

Gly Asp Glu Ala Ala Pro Gly Glu Leu Pro Tyr Gln Leu Ser Phe Gln
        35                  40                  45

Asp Leu Ser Tyr Gly Asp Pro Trp His Phe Cys Gly Ala Ser Ile Tyr
    50                  55                  60

Asn Glu Asn Trp Ala Ile Cys Ala Gly His Cys Val Ala Gly Glu Asp
65                  70                  75                  80
```

Met Asn Asn Pro Asp Tyr Leu Gln Val Val Ala Gly Glu His Asn Gln
            85                  90                  95

Asp Ile Val Glu Gly Asn Glu Gln Thr Ile Ile Leu Ser Lys Ile Ile
            100                 105                 110

Gln His Glu Gly Tyr Asn Ala Phe Thr Val Ser Asn Asp Ile Ser Val
            115                 120                 125

Leu Gln Leu Ser Gln Pro Leu Thr Phe Asn Asp Tyr Val Gln Pro Ile
            130                 135                 140

Ala Leu Pro Glu Ala Gly His Thr Ala Ser Gly Asp Cys Ile Val Ser
145                 150                 155                 160

Gly Trp Gly Thr Thr Ser Glu Gly Gly Asn Thr Pro Ser Val Leu Met
            165                 170                 175

Lys Val Ala Val Pro Val Val Thr Asp Glu Glu Cys Thr Asp Ala Tyr
            180                 185                 190

Gly Glu Gly Glu Ile Leu Asp Ser Met Ile Cys Ala Gly Leu Pro Glu
            195                 200                 205

Gly Gly Lys Asp Ser Cys Gln Gly Asp Ser Gly Gly Pro Phe Ala Cys
            210                 215                 220

Ser Asp Thr Gly Ser Pro Tyr Leu Ala Gly Val Val Ser Trp Gly Tyr
225                 230                 235                 240

Gly Cys Ala Arg Pro Asn Tyr Pro Gly Val Tyr Thr Glu Val Ser Tyr
            245                 250                 255

Phe Val Asp Trp Ile Met Thr Asn Thr Ala
            260                 265

<210> SEQ ID NO 5
<211> LENGTH: 23
<212> TYPE: PRT
<213> ORGANISM: Euphausia superba

<400> SEQUENCE: 5

Val Ala Val Pro Val Val Thr Asp Glu Glu Cys Thr Ala Ala Tyr Gly
1               5                   10                  15

Glu Gly Glu Ile Leu Asp Ser
            20

<210> SEQ ID NO 6
<211> LENGTH: 21
<212> TYPE: PRT
<213> ORGANISM: Euphausia superba

<400> SEQUENCE: 6

Lys Asp Ser Cys Gln Gly Asp Ser Gly Gly Pro Phe Ala Cys Ser Asp
1               5                   10                  15

Thr Gly Ser Pro Tyr
            20

<210> SEQ ID NO 7
<211> LENGTH: 16
<212> TYPE: PRT
<213> ORGANISM: Euphausia superba
<220> FEATURE:
<221> NAME/KEY: SITE
<222> LOCATION: (16)..(16)
<223> OTHER INFORMATION: Xaa can be any naturally occurring amino acid

<400> SEQUENCE: 7

Ile Val Gly Gly Asp Glu Ala Ala Pro Gly Glu Leu Pro Tyr Gln Xaa
1               5                   10                  15

```
<210> SEQ ID NO 8
<211> LENGTH: 36
<212> TYPE: PRT
<213> ORGANISM: Euphausia superba

<400> SEQUENCE: 8

Val Ala Ala Pro Val Val Thr Asp Glu Glu Ser Thr Asp Ala Tyr Gly
 1               5                  10                  15

Glu Gly Glu Ile Leu Asp Ser Met Ile Cys Ala Gly Leu Pro Glu Gly
            20                  25                  30

Gly Lys Asp Ser
        35

<210> SEQ ID NO 9
<211> LENGTH: 15
<212> TYPE: DNA
<213> ORGANISM: ARTIFICIAL SEQUENCE
<220> FEATURE:
<221> NAME/KEY: misc_feature
<222> LOCATION: (1)..(1)
<223> OTHER INFORMATION: synthesized, n is a, c, g, or t
<220> FEATURE:
<221> NAME/KEY: misc_feature
<222> LOCATION: (4)..(4)
<223> OTHER INFORMATION: synthesized, n is a, c, g, or t
<220> FEATURE:
<221> NAME/KEY: misc_feature
<222> LOCATION: (7)..(7)
<223> OTHER INFORMATION: synthesized, n is a, c, g, or t

<400> SEQUENCE: 9
nagnccngcg atcat                                              15

<210> SEQ ID NO 10
<211> LENGTH: 26
<212> TYPE: DNA
<213> ORGANISM: ARTIFICIAL SEQUENCE
<220> FEATURE:
<223> OTHER INFORMATION: oligonucleotide primer

<400> SEQUENCE: 10
ccagagtcac cctggcacga gtcctt                                  26

<210> SEQ ID NO 11
<211> LENGTH: 20
<212> TYPE: DNA
<213> ORGANISM: ARTIFICIAL SEQUENCE
<220> FEATURE:
<223> OTHER INFORMATION: oligonucleotide primer

<400> SEQUENCE: 11
atctgcatcg tgtccggttg                                         20

<210> SEQ ID NO 12
<211> LENGTH: 23
<212> TYPE: DNA
<213> ORGANISM: ARTIFICIAL SEQUENCE
<220> FEATURE:
<223> OTHER INFORMATION: oligonucleotide primer

<400> SEQUENCE: 12
cgcggtctca acaagatcgt cgg                                     23

<210> SEQ ID NO 13
<211> LENGTH: 19
<212> TYPE: DNA
```

```
<213> ORGANISM: ARTIFICIAL SEQUENCE
<220> FEATURE:
<223> OTHER INFORMATION: primer

<400> SEQUENCE: 13
cattggagac agtaaatgc                                                   19

<210> SEQ ID NO 14
<211> LENGTH: 22
<212> TYPE: DNA
<213> ORGANISM: ARTIFICIAL SEQUENCE
<220> FEATURE:
<223> OTHER INFORMATION: primer

<400> SEQUENCE: 14
tgatggtctg ctcattgcct tc                                               22

<210> SEQ ID NO 15
<211> LENGTH: 22
<212> TYPE: DNA
<213> ORGANISM: ARTIFICIAL SEQUENCE
<220> FEATURE:
<223> OTHER INFORMATION: primer

<400> SEQUENCE: 15
tgcatttact gtctccaatg ac                                               22

<210> SEQ ID NO 16
<211> LENGTH: 19
<212> TYPE: DNA
<213> ORGANISM: ARTIFICIAL SEQUENCE
<220> FEATURE:
<223> OTHER INFORMATION: primer

<400> SEQUENCE: 16
atgaagggat ttgtgatct                                                   19

<210> SEQ ID NO 17
<211> LENGTH: 20
<212> TYPE: DNA
<213> ORGANISM: ARTIFICIAL SEQUENCE
<220> FEATURE:
<223> OTHER INFORMATION: primer

<400> SEQUENCE: 17
tgcggtgtta gtcataatcc                                                  20
```

PROTEIN AND NUCLEIC ACID SEQUENCE ENCODING A KRILL-DERIVED COLD ADAPTED TRYPSIN-LIKE ACTIVITY ENZYME

BACKGROUND OF THE INVENTION

1. Field of the Invention

The present invention relates to purified nucleic acids encoding antartic krill (*Euphausia superba*) derived enzymes such as proteinases, which can be a protein, and to purified polypeptides that have high proteolitytic activity and belong to the family of serine trypsin like enzymes. The present invention also relates to a protein having cold adapted activity, especially specific activity in the range of 4–50° C. In addition, the present invention relates to a DNA construct comprising a DNA sequence encoding the cold adapted trypsin protease, and a cell including the DNA construct. Furthermore, the present invention relates to a method of preparing the cold adapted trypsin protease by using recombinant DNA techniques.

2. Description of the Prior Art

The trypsin/chymotrypsin-like serine protease (S1) family plays roles in a multitude of diverse physiological processes, including digestive processes and regulatory amplification cascades through the proteolytic activation of inactive zymogen precursors, including its self activation. In addition to activating zymogen proteases, the trypsin/chymotrypsin-like serine protease can digest almost any protein with basic amino acids as part of its sequence and has thus become a common protein-chemistry reagent.

Trypsin proteases are used in numerous and varied industrial contexts and commercial purposes including laundry detergents, food processing, drugs, and skin care products. In laundry detergents, the protease is employed to break down organic or poorly soluble compounds to more soluble forms that can be more easily dissolved in detergent and water. Examples of food processing include tenderizing meats and maturing cheese. Proteases may be used in skin care field to remove scales on the skin surface that build up due to an imbalance in the rate of desquamation. In the case of drugs, several oral enzyme therapies that include trypsin as one component have shown promise in easing inflammation and in treating some cancers.

Common proteases used in some of these applications are derived from prokaryotic or eukaryotic cells that are easily grown for industrial manufacture of their enzymes. For example, a common species used is *Bacillus* as described in U.S. Pat. No. 5,217,878. Alternatively, U.S. Pat. No. 5,278,062 describes serine proteases isolated from a fungus, *Tritirachium album*, for use in laundry detergent compositions. The advent of recombinant technology allows expression of any species' proteins in a host suitable for industrial manufacturing. The majority of the commercially available proteases used in detergent application have high optimal temperatures, for example 60° C.

Other enzymes with cold adapted trypsin like activity and from vertebrates (Atlantic salmon, Antarctic fish, Atlantic cod and pufferfish) have been previously characterized (Schroder, H., Willassen, Nils., Smalas, Arne. (1999) Extremophiles 3:205–219). But all these proteins have high homology and low thermal stability at ambient temperatures.

Therefore, there is a need for a new protease, in this case trypsin-like protease, that works at ambient temperatures.

SUMMARY OF THE INVENTION

One preferred embodiment of the present invention is a substantially pure nucleic acid comprising a nucleic acid encoding a polypeptide having at least about 85% homology (such as identity or similarity) to a krill-derived cold adapted trypsin protein or a reference protein, such as the polypeptide of SEQ ID NOS: 3 or 4, and more preferably, at least about 90% homology. These levels of homology (such as identity or similarity) apply to all embodiments of the invention.

In certain preferred embodiments, the substantially pure nucleic acid comprises an engineered nucleic acid variant encoding a polypeptide differing from a reference protein or a krill-derived cold adapted trypsin protein or its isoforms by no more than about 30 amino acid substitutions, and more preferably, no more than about 20 amino acid substitutions. Preferably, the engineered substitutions cause a conservative substitution in the amino acid sequence of a reference sequence or a cold adapted protein.

The invention additionally includes vectors capable of reproducing in a cell (such as a eukaryotic or prokaryotic cell) having a nucleic acid equal to sequence of SEQ ID NOS: 1 or 2 as well as transformed cells having such nucleic acid.

Another preferred embodiment is a transformed cell (such as a prokaryotic or eukaryotic cell) comprising a nucleic acid encoding a polypeptide having at least about 85% homology to a reference sequence or a krill-derived cold adapted trypsin protein. Preferably, the transformed cell expresses one of the enzymes described herein.

Yet another preferred embodiment is a vector capable of reproducing in a cell such as a eukaryotic or prokaryotic cell. The vector comprises a nucleic acid encoding a polypeptide having at least about 85% homology to a reference sequence or a krill-derived cold adapted trypsin protein comprising SEQ ID NOS: 3 or 4. Preferably, the inventive vector codes for expression, intracellularly or extracellularly, of the cold adapted trypsin protein described herein.

Another embodiment of the present invention is a polypeptide comprising a substantially pure isoform of a reference sequence or a krill-derived cold adapted trypsin protein or engineered variant thereof, and preferably, a polypeptide comprising SEQ ID NOS: 3 or 4.

The invention further provides a cleaning or detergent composition comprising the polypeptide or the cold adapted trypsin protein of the invention.

Yet another preferred embodiment is a method of preparing an enzyme such as a cold adapted trypsin, wherein the protein has at least about 85% homology to a reference sequence or a krill-derived multifunctional protein. Such method comprises 1. Constructing a recombinant chimeric expression vector, comprising a nucleic acid sequence of the present invention such as SEQ ID NOS: 1 or 2;
2. Transforming an appropriate eukaryotic or prokaryotic host cell with the expression vector for expressing intracellularly or extracellularly a nucleic acid encoding the protein; and
3. Growing the transformed cell in culture and isolating the protein from the transformed cell or the culture medium.

These together with other objects and advantages which will become subsequently apparent reside in the details construction and operation as more fully hereinafter described and claimed.

DETAILED DESCRIPTION OF THE PREFERRED EMBODIMENTS

Although only the preferred embodiments of the invention are explained in detail, it is to be understood that the invention is not limited in its scope to the details set forth in the following description. The invention is capable of other embodiments and of being practiced or carried out in various ways. Also, in describing the preferred embodiments, specific terminology will be resorted to for the sake of clarity. It is to be understood that each specific term includes all technical equivalents which operate in a similar manner to accomplish a similar purpose.

For the purposes of this application, the terms listed below shall have the following meaning:

"Isoform" refers to a naturally occurring sequence variant of a substantially homologous protein within the same organism. Preferably, the isoform shares at least about 85% identity and more preferably, at least about 90% identity with the amino acid sequence shown as amino acid residues (AA) 30 to 266 of SEQ. ID NO: 3 or sequence shown as AA 30 to 266 of SEQ. ID NO: 4.

"Krill derived cold adapted trypsin like acticity protein" refers to a cold adapted trypsin protein having the same sequence as a protein isolated from krill and having the properties of the protein described in the section entitled "Preferred Characteristics of the Cold Adapted Trypsin Protein." The amino acid sequence included in SEQ ID NO:3, SEQ ID NO:4 or other isoforms thereof or chimeric polypeptides thereof are examples of krill-derived cold adapted trypsin-like activity proteins.

"Percent sequence identity" refers to the percentage of two sequences that are deemed identical, homologous or similar within the skill in the art. To determine the percent identity of two amino acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). Alignment for purposes of determining percent amino acid sequence identity can be achieved in various ways that are within the skill in the art, for example, using publicly available computer software such as BLAST-2 software that are set to their default parameters. Those skilled in the art can determine appropriate parameters for measuring alignment, including any algorithms needed to achieve maximal alignment over the full length of the sequences being compared. The ClustalW (1.60) alignment method is used in this application.

Nucleic Acids and Polypeptides

The nucleic acid embodiments of the invention are preferably deoxyribonucleic acids (DNAs), both single- and double-stranded, and most preferably double-stranded deoxyribonucleic acids. However, they can also be, without limitation, ribonucleic acids (RNAs), as well as hybrid RNA:DNA double-stranded molecules.

Nucleic acids encoding a krill derived cold adapted protein, whether native or synthetic, RNA, DNA, or cDNA, that encode the protein, or the complementary strand thereof, including but not limited to nucleic acid found in a cold adapted trypsin protein-expressing organism. For recombinant expression purposes, codon usage preferences for the organism in which such a nucleic acid is to be expressed are advantageously considered in designing a synthetic cold adapted trypsin protein-encoding nucleic acid.

The nucleic acid sequences can be further mutated, for example, to incorporate useful restriction sites. See Sambrook et al. Molecular Cloning, a Laboratory Manual (Cold Spring Harbor Press, 1989). Such restriction sites can be used to create "cassettes", or regions of nucleic acid sequence that are easily substituted using restriction enzymes and ligation reactions. The cassettes can be used to substitute synthetic sequences encoding mutated cold adapted trypsin protein amino acid sequences.

The nucleic acid sequences of the present invention can encode, for example, one of several isoforms of a krill-derived protein. SEQ ID NOS: 3 and 4 represent two isoforms that share about 98% identity with each other in overlapping amino acids.

These two isoforms additionally contain a pro-protein segment. The pro-protein segment is the segment of the protein, that is present in the precursor protein but absent in the mature protein. In the first isoform, the pro-protein segment has the following sequence, which corresponds to amino acid residues 1–29 in the first isoform, SEQ ID NO:3:Met Lys Gly Phe Val Ile Cys Leu Leu Val Ala Gly Ala Cys Ala Ala Pro Ser Arg Lys Pro Thr Phe Arg Lys Asp Leu Asn Lys. The second isoform has a pro-protein segment with the following sequence, which corresponds to amino acid residues 1–29 in SEQ ID NO:4:Met Lys Gly Phe Val Ile Cys Leu Leu Val Ala Gly Ala Cys Ala Ala Pro Ser Arg Lys Pro Thr Phe Arg Arg Gly Leu Asn Lys. The remaining amino acid sequences of these polypeptides (other than the pro-protein segment) represent the mature protein.

The amino acid sequence forming a synthetic cold adapted protein preferably includes an enzymatically active segment of a krill-derived protein, such as amino acids residues 30–266 of SEQ ID NO: 3, particularly including the histidine at residue 74, the aspartic acid at residue 125 and the serine at residue 225, which are implicated in the catalytic mechanism of serine proteases. Thus, the protein need not include the pro-protein segment that is present in a krill-derived protein before cellular processing occurs, although the pro-protein segment are not preferably present.

Preferably, the nucleic acids will encode polypeptides having at least 80% homology, more preferably, at least 85% homology, even more preferably, at least about 90% homology, and most preferably at least 95% homology to a reference protein or a krill-derived cold adapted trypsin protein, such as the polypeptides of SEQ ID NO:3 or SEQ ID NO:4, or other naturally occurring isoforms.

The mature protein of the polypeptide of SEQ ID NO: 3 is about 79% identical to the trypsin serine proteinase in the shrimp *Penaeus vannamei* according to the sequence provided by Genbank (Mountain View, Calif.), database acquisition no. 1086280, and about 68% identical to the serine proteinase in the crayfish *Astacus fluviatilis*, according to the sequence provided by Genbank, database acquisition no. P00765. and about 66% identical to the collagenolytic serine proteinase in the King crab *Paralithodes camtschaticus*, according to the sequence provided by Genbank, database acquisition no. AAL67442. Preferably, the nucleic acids encoding polypeptides having cold adapted trypsin activity are less than about 80% identical to the above-identified proteinases of *Penaeus vannamei, Astacus fluviatilis* or *Paralithodes camtschaticus*.

The cold adapted trypsin protein-encoding sequence can be, for instance, substantially or fully synthetic. For recombinant expression purposes, codon usage preferences for the organism in which such a nucleic acid is to be expressed are advantageously considered in designing a synthetic cold adapted protein-encoding nucleic acid. Since the nucleic acid code is degenerate, numerous nucleic acid sequences can be used to create the same amino acid sequence. This natrual "degeneracy" or "redundancy" of genetic code is well known in the art. It will thus be appreciated that the nucleic acid sequences shown in Sequence Listing provide only an example within a large but definite group of nucleic acid sequecnes that will encode the relevant polypeptides as described herein.

Polypeptides of the present invention preferably include all polypeptides encoded by the nucleic acids having the sequence identical to SEQ ID NOS: 1 or 2 or their degenerate variants thereof, and all polypeptides comprising the amino acid sequences shown as AA30–266 of SEQ ID NO: 3 or sequence shown as AA30–266 of SEQ ID NO: 4, as well as all obvious variants of these peptides that are within the art to make and use. In addition, the polypeptides according to the present invention have, preferably at least about 85% sequence identity, also preferably at least about 90% sequence identity, more preferably at least about 95% sequence identity, even preferably at least about 96% sequence identity, still preferably at least about 97% sequence identity, yet preferably at least about 98% sequence identity, and most preferably at least about 99% sequence identity to the amino acid sequence selected from AA30–266 of SEQ ID NO: 3 or sequence shown as AA30–266 of SEQ ID NO: 4.

Methods of Synthesizing Polypeptides

Expression Vectors

The present invention also relates to recombinant expression vectors comprising a nucleic acid sequence of the present invention, a promoter, and transcriptional and translational stop signals. The nucleic acid sequence of the present invention may be expressed by inserting the nucleic acid sequence or a nucleic acid construct comprising the sequence as identified in SEQ ID NOS: 1 or 2 into an appropriate vector for expression. In creating the expression vector, the coding sequence as identified in SEQ ID NOS. 1 or 2 is located in the vector so that it is operably linked with the appropriate control sequences for expression.

The recombinant expression vector may be any vector (e.g., a plasmid) which can be conveniently subjected to recombinant DNA procedures and can bring about the expression of the nucleic acid sequence. The choice of the vector will typically depend on the compatibility of the vector with the host cell into which the vector is introduced. The vectors may be linear or closed circular plasmids.

The vector may be an autonomously replicating vector, i.e., a vector which exists as an extra chromosomal entity and its replication is independent of chromosomal replication, e.g., a plasmid, an extra chromosomal element, a mini chromosome, or an artificial chromosome. The vector may contain any means for assuring self-replication. Alternatively, the vector may be one which, when introduced into the host cell, is integrated into the host cell's genome and replicated together with the chromosome(s). Furthermore, a single vector or plasmid or two or more vectors or plasmids which together contain the total DNA to be introduced into the genome of the host cell, or a transposon may be used.

The vectors of the present invention preferably contain one or more selectable markers which permit easy selection of transformed cells. A selectable marker is a gene whose expression product provides for biocide or viral resistance, resistance to heavy metals, prototrophy to auxotrophs, and the like. Examples of bacterial selectable markers are the dal genes from *Bacillus subtilis* or *Bacillus licheniformis*, or markers which confer antibiotic resistance such as ampicillin, kanamycin, chloramphenicol or tetracycline resistance. Suitable markers for yeast host cells are ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hygB (hygromycin phosphotransferase), niaD (nitrate reductase), pyrG (orotidine-5'-phosphate decarboxylase), sC (sulfate adenyltransferase), trpC (anthranilate synthase), as well as equivalents thereof. The amdS and pyrG genes of *Aspergillus nidulans* or *Aspergillus oryzae* and the bar gene of *Streptomyces hygroscopicus* are preferred for use in an *Aspergillus* cell.

The vectors of the present invention preferably contain an element(s) that permits stable integration of the vector into the host cell's genome or autonomous replication of the vector in the cell independent of the genome.

For integration into the host cell genome, the vector may rely on the nucleic acid sequence encoding the polypeptide or any other element of the vector for stable integration of the vector into the genome by homologous or non-homologous recombination. Alternatively, the vector may contain additional nucleic acid sequences for directing integration by homologous recombination into the genome of the host cell. The additional nucleic acid sequences enable the vector to be integrated into the host cell genome at a precise location(s) in the chromosome(s). To increase the likelihood of integration at a precise location, the integrational elements should preferably contain a sufficient number of nucleic acids, such as 100 to 1,500 base pairs, preferably 400 to 1,500 base pairs, and most preferably 800 to 1,500 base pairs, which are highly homologous with the corresponding target sequence to enhance the probability of homologous recombination. The integrational elements may be any sequence that is homologous with the target sequence in the genome of the host cell. Furthermore, the integrational elements may be non-encoding or encoding nucleic acid sequences. On the other hand, the vector may be integrated into the genome of the host cell by non-homologous recombination.

For autonomous replication, the vector may further comprise an origin of replication enabling the vector to replicate autonomously in the host cell in question. Examples of bacterial origins of replication are the origins of replication of plasmids pBR322, pUC19, pACYC177, and pACYC184 permitting replication in *E. coli*, and pUB110, pE194, pTA1060, and pAM.beta.1 permitting replication in *Bacillus*. Examples of origins of replication for use in a yeast host cell are the 2 micron origin of replication, ARS1, ARS4, the combination of ARS1 and CEN3, and the combination of ARS4 and CEN6.

More than one copy of a nucleic acid sequence of the present invention may be inserted into the host cell to increase production of the gene product. An increase in the copy number of the nucleic acid sequence can be obtained by integrating at least one additional copy of the sequence into the host cell genome or by including an amplifiable selectable marker gene with the nucleic acid sequence where cells containing amplified copies of the selectable marker gene, and thereby additional copies of the nucleic acid sequence, can be selected by cultivating the cells in the presence of the appropriate selectable agent.

The procedures used to ligate the elements described above to construct the recombinant expression vectors of the present invention are well known to one of ordinary skill in the art (see, e.g., Sambrook et al., 1989).

Host Cells

The present invention also relates to recombinant host cells, comprising a nucleic acid sequence of the present invention for the recombinant production of the polypeptides.

A vector comprising a nucleic acid sequence of the present invention is introduced into a host cell so that the vector is maintained as a chromosomal integrant or as a self-replicating extra-chromosomal vector as described earlier. The choice of a host cell will, to a large extent, depend upon the gene encoding the polypeptide and its source.

The host cell may be a unicellular microorganism, e.g., a prokaryote, or a non-unicellular microorganism, e.g., a eukaryote.

Useful unicellular cells are bacterial cells such as gram positive bacteria including, but not limited to, a *Bacillus* cell, e.g., *Bacillus alkalophilus, Bacillus amyloliquefaciens, Bacillus brevis, Bacillus circulans, Bacillus clausii, Bacillus coagulans, Bacillus lautus, Bacillus lentus, Bacillus licheniformis, Bacillus megaterium, Bacillus stearothermophilus, Bacillus subtilis,* and *Bacillus thuringiensis*; or a *Streptomyces* cell, e.g., *Streptomyces lividans* or *Streptomyces murinus*, or gram negative bacteria such as *E. coli* and *Pseudomonas* sp. In a preferred embodiment, the bacterial host cell is a *Bacillus lentus, Bacillus licheniformis, Bacillus stearothermophilus,* or *Bacillus subtilis* cell. In another preferred embodiment, the *Bacillus* cell is an alkalophilic *Bacillus*.

The introduction of a vector into a bacterial host cell may, for instance, be achieved by protoplast transformation through electroporation or conjugation, using competent cells.

The host cell may be a eukaryote, such as a mammalian, insect, plant, or fungal cell. In a preferred embodiment, the host cell is a fungal cell. "Fungi" as used herein includes the phyla *Ascomycota, Basidiomycota, Chytridiomycota,* and *Zygomycota* as well as the *Oomycota* and all mitosporic fingi.

In a more preferred embodiment, the fungal host cell is a yeast cell. "Yeast" as used herein includes ascosporogenous yeast (Endomycetales), basidiosporogenous yeast, and yeast belonging to the Fungi Imperfecti (Blastomycetes).

In an even more preferred embodiment, the yeast host cell is a *Candida, Hansenula, Kluyveromyces, Pichia, Saccharomyces, Schizosaccharomyces,* or *Yarrowia* cell.

In a most preferred embodiment, the yeast host cell is a *Saccharomyces carlsbergensis, Saccharomyces cerevisiae, Saccharomyces diastaticus, Saccharomyces douglasii, Saccharomyces kluyveri, Saccharomyces norbensis* or *Saccharomyces oviformis* cell.

Production

The present invention also relates to a method for producing a polypeptide of the invention, the method comprising (a) cultivating a recombinant host cell as described above under conditions conducive to the production of the polypeptide, and (b) recovering the polypeptide from the cells and/or the culture medium.

In the production methods of the present invention, the cells are cultivated in a nutrient medium suitable for production of the polypeptide using methods known in the art. For example, the cell may be cultivated by shake flask cultivation, small-scale or large-scale fermentation (including continuous, batch, fed-batch, or solid state fermentations) in laboratory or industrial fomenters performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions. If the polypeptide is secreted into the nutrient medium, the polypeptide can be recovered directly from the medium. If the polypeptide is not secreted, it can be recovered from cell lysates.

The polypeptides may be detected using methods known in the art that are specific for the polypeptides. These detection methods may include use of specific antibodies, formation of an enzyme product, or disappearance of an enzyme substrate.

The resulting polypeptide may be recovered by methods known in the art. For example, the polypeptide may be recovered from the nutrient medium by conventional procedures including, but not limited to, centrifugation, filtration, extraction, spray-drying, evaporation, or precipitation.

The polypeptides of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., Protein Purification, J.-C. Janson and Lars Ryden, editors, VCH Publishers, New York, 1989). The polypeptides of the present invention may need additional purification. Techniques are applied as needed, including without limitation, FPLC (Pharmacia, Uppsala, Sweden), HPLC (e.g., using gel filtration, reverse-phase or mildly hydrophobic columns).

Preferred Characteristics of the Cold Adapted Trypsin Protein

Antartic Krill, including without limitation krill of the species *Euphasia superba*, is the preferred source of krill-derived cold adapted trypsin proteins.

Preferably, the protein has a molecular weight between about 17 kd and about 26 kd, and more preferably from about 24 kd to about 26 kd, and most preferably about 25 kd, as determined by sodium dodecyl sulfate ("SDS") polyacrylamide gel electrophoresis ("PAGE"). Further, the protein preferably has substantial homology to a krill-derived cold adapted trypsin protein. Preferred proteins are hydrolases, and preferably, proteases.

Protease activity can be determined by incubating a protein preparation with casein (concentration 2% w/v in Tris HCl 20 mM, pH 7.5) at 20° C. for 20 minutes and measuring the release of amino acids or peptides by measuring the increase in colorometrically determinable amino groups whih Folin-Ciocalteu at 6,6% v/v in the presence of 150 Mm NaOH.

Trypsin activity can be determined by the Erlanger et al. method, that consists of the measurement of the degradation of BAPNA in 1 mM of Tris HCl pH 8.2 and 20 mM of $CaCl_2$ in the presence of 0.1% V/V of DMS for 20 minutes at 20° C.

Preferably, the pH optimum of the cold adapted protein is substrate dependent. For the substrate casein, the pH optimum is preferably from about 5 to about 12, more preferably, from about 7 to about 10. For the substrate BAPNA, the pH optimum is preferably from about 7 to about 10, more preferably in excess of about 9.0.

Preferably, the cold adapted trypsin protein has a temperature optimum for activity against casein and against BAPNA of between about 40° C. and about 50° C. The degradation efficiency of the cold adapted proteinases was found to be approximately 2 and 3 times higher compared with porcine trypsin at 50° C. and 20° C., respectively, and show activity at 4° C., using both substrates.

Use in Detergent

The polypeptide of the invention may be added to and thus become a component of a detergent composition (U.S. Pat. No. 5,693,520).

The detergent composition of the invention may for example be formulated as a hand or machine laundry detergent composition that includes a laundry additive composition suitable for pre-treatment of stained fabrics, and a rinse added fabric softener composition. Alternatively, the detergent composition of the present invention may be used in general household hard surface cleaning operations, or be formulated for hand or machine dishwashing operations.

In a specific aspect, the invention provides a detergent additive comprising the enzyme of the invention. The detergent additive as well as the detergent composition may comprise one or more other enzymes such as a lipase, a cutinase, an amylase, a carbohydrase, a cellulase, a pectinase, a mannanase, an arabinase, a galactanase, a xylanase, an oxidase, e.g., a laccase, and/or a peroxidase.

In general the properties of the chosen enzyme(s) should be compatible with the selected detergent, (i.e. pH-optimum, compatibility with other enzymatic and non-enzymatic ingredients, etc.), and the enzyme(s) should be present in effective amounts.

Other Uses

Trypsin is widely used in the processing of biopharmaceutical proteins, such as in the production of insulin from proinsulin (Kemmler, W., Peterson, J. and Steiner, D. (1971) Biol. Chem. 246: 6786–6791).

Oral enzyme therapies that include trypsin as one component have show promise in easing inflammation and in treating some cancer (Leiper, J. and Saller, R (2000) Drugs 59, 769–780).

The present invention may also be used in contact lens cleaning and disinfecting systems (U.S. Pat. No. 6,358,897, U.S. Pat. No. 6,139,646).

In addition, the present invention may be used in topical treatments, in the treating of skin scaring and skin infection (Jung H. (1998) Facial Plast Surg; 14(4): 255–257).

In the food industry, for example aminopeptidases have been used to increase the speed in the cheese maturing process.

Materials and Methods

The present invention is further exemplified by the following non-limiting examples.

EXAMPLE 1

Protein Purification and Partial Amino Acid Sequencing

Briefly, the krill was autolysed for 48 hours at 20° C., the liquid fraction was precipitated with ammonium sulfate and desalted in a Sephadex G-25 column, and subjected to a anion exchange chromatography with Q-sepharose Fast Flow, four fraction with protease activity were purified in benzamidine-Sepharose affinity chromatography, to this partially purified protein a trypsin activity assay was carried out at 20° C., the fraction with the higher activity protein was sequenced by The Pasteur Institute (SEQ ID NOS:5,6,7) and Chiron Corporation (SEQ ID NO:8).

EXAMPLE 2 cDNA Cloning of Characterized and Sequenced Protein of the Invention

The RNA was insolated from frozen (liquid nitrogen) antartic krill, with Trizol® reagent using the manufacturer's specifications. For mRNA purification, total RNA was treated with the Oligotex® kit (Qiagen). The mRNA insolate was used in a reverse transcription polymerase chain reaction (RT-PCR). For this procedure, four specific and degenerate oligonucleotide primers (SEQ ID NOS: 9,10,11,12) were designed based on the partial amino acid sequences (SEQ ID NOS: 5,6,7,8). The amplifications were cloned in a pGEM-T system (Promega) and selected clones were automatically sequenced. Nucleic acid sequences were analyzed for searching homology with the amino acid of the purified trypsin. The sequence of the higher homology clone was used for design of a new set of specific primers used in a 5' RACE system for rapid amplification of cDNA ends kit (SEQ ID NOS: 13, 14) and a 3' RACE system for rapid amplification of cDNA ends kit (SEQ ID NO: 15), both provided by Invitrogen. The amplifications of this PCR were cloned and sequenced.

EXAMPLE 3

Construction of Expression Vector and Expression of the Protein of the Invention With the sequences obtained with the 5' and 3'RACE system, two primers (SEQ ID NOS:16, 17) were designed and a final RT-PCR was carried out. In addition, cloning and sequencing of the complete gene which encodes the purified trypsin were completed. Eight clones were analyzed, representing two isoforms of the same gene (SEQ ID NOS: 1 and2). The cold adapted trypsin protein was expressed in *E. coli* as follows by using the Eco RI and Xho I sites of a pET22b vector provided by Novagen. The pET vector places the recombinant protein under the control of bacteriophage T7 transcription and translation signals. Once established in a non-expression host, *E. coli* DH5, the plasmid was then transferred to an expression host, *E. coli* BL21 (DE3) pLYS S having a chromosomal copy of the T7 polymerase gene under lacUV5 control. Expression was induced by the addition of IPTG.

Sequences

The nucleic acid sequences described herein, and consequently the protein sequences derived there from, have been carefully sequenced. However, those of ordinary skill will recognize that nucleic acid sequencing technology can be susceptible to some inadvertent error. Those of ordinary skill in the relevant arts are capable of validating or correcting these sequences based on the ample description herein of methods of isolating the nucleic acid sequences in question and such modifications that are made readily available by the present disclosure are encompassed by the present invention. Furthermore, those sequences reported herein are believed to define functional biological macromolecules within the invention whether or not later clarifying studies identify sequencing errors.

What is claimed is:

1. An isolated polypeptide having an amino acid sequence which has at least 95% sequence identity with the amino acid sequence shown as amino acid residues 30 to 266 of SEQ ID NO:3 and having serine protease activity.

2. An isolated polypeptide having an amino acid sequence which has at least 95% sequence identity with the amino acid sequence shown as amino acid residues 30 to 266 of SEQ ID NO:4 and having serine protease activity.

3. The polypeptide of claim 1, having an amino acid sequence which has at least 96% sequence identity with the amino acid sequence shown as amino acid residues 30 to 266 of SEQ ID NO:3.

4. The polypeptide of claim 2, having an amino acid sequence which has at least 96% sequence identity with the amino acid sequence shown as amino acid residues 30 to 266 of SEQ ID NO:4.

5. The polypeptide of claim 1, having an amino acid sequence which has at least 97% sequence identity with the amino acid sequence shown as amino acid residues 30 to 266 of SEQ ID NO:3.

6. The polypeptide of claim 2, having an amino acid sequence which has at least 97% sequence identity with the amino acid sequence shown as amino acid residues 30 to 266 of SEQ ID NO:4.

7. The polypeptide of claim 1, having an amino acid sequence which has at least 98% sequence identity with the amino acid sequence shown as amino acid residues 30 to 266 of SEQ ID NO:3.

8. The polypeptide of claim 2, having an amino acid sequence which has at least 98% sequence identity with the amino acid sequence shown as amino acid residues 30 to 266 of SEQ ID NO:4.

9. The polypeptide of claim 1, having an amino acid sequence which has at least 99% sequence identity with the amino acid sequence shown as amino acid residues 30 to 266 of SEQ ID NO:3.

10. The polypeptide of claim 2, having an amino acid sequence which has at least 99% sequence identity with the amino acid sequence shown as amino acid residues 30 to 266 of SEQ ID NO:4.

11. The polypeptide of claim 1, comprising the amino acid sequence shown as amino acid residues 30–266 of SEQ ID NO:3.

12. The polypeptide of claim 2, comprising the amino acid sequence shown as amino acid residues 30–266 of SEQ ID NO:4.

13. The polypeptide of claim 12 or claim 11 encoded by an isolated nucleic acid comprising at least one of:

(a) a sequence identical to SEQ ID NO: 1; or (b) a sequence identical to SEQ ID NO: 2.

14. A cleaning or detergent composition comprising an effective amount of the polypeptide as defined in claims 2 or 1.

* * * * *